United States Patent [19]
Georgiev et al.

[11] Patent Number: 4,767,867
[45] Date of Patent: Aug. 30, 1988

[54] 5-(ALKOXYALKYL)-3-PHENYL-3-(1H-IMIDAZOL-1-YLMETHYL)-2-METHYLISOXAZOLIDINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 36,832

[22] Filed: Apr. 10, 1987

[51] Int. Cl.[4] .................. A01N 43/52; C07D 233/60
[52] U.S. Cl. ...................................... 548/240; 548/341
[58] Field of Search ......................................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |

OTHER PUBLICATIONS

Kelly, R. C. et al., Chem. Abstract 93:114498u (1980), Abstracting German Offen. 2,918,878 (Nov. 22, 1979).
Haken, P. T. et al., Chem. Abstract 93:132471i: (1980), Abstracting Brit. Pat. Appln. 2,024,218 (Jan. 9, 1980).
Takahi, Y. et al., Chem. Abstract 81:22233c (1974) Abstracting Japan Kokai 7399,336 (Dec. 15, 1973).
Boyce, C. B. et al., Chem. Abstract 87:23258a (1977), Abstracting German Offen. 2,639,189 (Mar. 10, 1977).
Funaki, Y. et al., Chem. Abstract 92:128915u (1980), Abstracting Japan Kokai 79, 76,579 (Jun. 19, 1979).
Sokolov, S. V. et al., Chemical Abstract 55:7399 (1961) Abstracting "Isoxazole Compounds III. Synthesis of Some Isoxazolylazoles", Zhur, Obshchei Khim. 30 pp. 1781–1787 (1960).
Kano, H. et al., Chem. Abstract 62:9139A (1965) Abstracting French 1,376,432 (Oct. 23, 1964).
Kano, H. et al., Chem. Abstract 63:8367a (1965) Abstracting French 1,380,177 (Nov. 27, 1964).

Primary Examiner—Donald G. Daus
Assistant Examiner—Mark W. Noel

[57] ABSTRACT 5-(Hydroxy or alkoxyalkyl)-3-phenyl-3-(1H-imidazol-1-ylmethyl)-2-methylisoxazolidines and related derivatives in which hydrogens of the phenyl ring are replaced by halogen, lower alkyl or lower alkoxy groups are useful as antifungal agents.

12 Claims, No Drawings

5-(ALKOXYALKYL)-3-PHENYL-3-(1H-IMIDAZOL-1-YLMETHYL)-2-METHYLISOXAZOLIDINES

BACKGROUND OF THE INVENTION

This invention relates generally to substituted 2-methylisoxazolidines and more specifically to 5-(hydroxy or alkoxyalkyl)-3-phenyl-3-(1H-imidazol-1-ylmethyl)-2-methylisoxazolidines and related derivatives which are useful as antifungal agents.

BRIEF SUMMARY OF THE INVENTION

In accordance with this invention there are provided compounds of the formula:

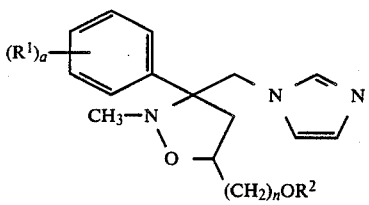

and the pharmaceutically acceptable acid addition salts thereof, in the form of their enantiomers or mixtures of their enantiomers including diastereoisomeric pairs of such enantiomers,
wherein,
a=1 or 2
$R^1$ is selected from hydrogen, lower alkyl, lower alkoxy, halogen and combinations thereof, provided that the ortho position is hydrogen,
$R^2$ is selected from hydrogen, lower alkyl, mono- or dihydroxy-substituted lower alkyl, allyl, cyclohexyl, lower alkyl-substituted cyclohexyl, methanesulfonyl and (halophenyl)methyl, and
the alkyl moiety $(CH_2)_n$ represents a branched or unbranched chain where n=1 to 4.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 5 and 8–10 below were found to have good to moderate inhibitory activity against a variety of organisms including trichophyon mentagrophytes, trichophyton rubrum, trichophyton tonsurans, trichophyton schoenleinii, epidermophyton floccosum, microporum canis and candida stellatoidea (minimum inhibitory concentration, MIC, of <0.2 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

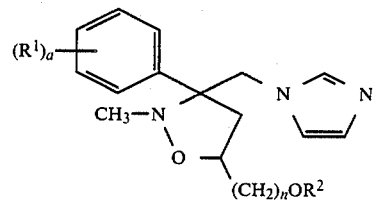

and the pharmaceutically acceptable acid addition salts thereof, in the form of their enantiomers or mixtures of their enantiomers including diastereoisomeric pairs of such enantiomers,
wherein;
a=1 or 2
$R^1$ is selected from hydrogen, lower alkyl, lower alkoxy, halogen, and combinations thereof, provided that the ortho position is hydrogen,
$R^2$ is selected from hydrogen, lower alkyl, mono- or dihydroxy-substituted lower alkyl, allyl, cyclohexyl, lower alkyl-substituted cyclohexyl, methanesulfonyl and (halophenyl)methyl, and
the alkyl moiety $(CH_2)_n$ represents branched or unbranched chain where n=1 to 4.

By halogen is meant chlorine, bromine, fluorine and iodine with chlorine and fluorine being preferred. By lower alkyl is meant groups containing one to four (1–4) carbons and by lower alkoxy is meant groups containing one to six (1–6) carbons. In either case such groups with three or more carbons can have a branched or unbranched chain. Compounds having ortho substitution of the 3-phenyl group were not prepared probably due to steric hindrance.

The 5-(hydroxy or alkoxyalkyl)-3-phenyl-3-(1H-imidazol-1-yl-methyl)-2-methylisoxazolidines of the invention are obtained as mixtures of cis- and trans-diastereomers due to the presence in the isoxazolidine ring of two asymmetric carbon atoms. The diastereomeric mixture is conveniently separated by flash-chromatography on silica gel using halogenated hydrocarbons (preferably dichloromethane and chloroform), alkanols (preferably methanol and ethanol), ethyl acetate and such as eluents. The eluents may be utilized alone or in combination such as the ones comprised of 95–99% by volume halogenated hydrocarbon and 1–5% by volume alkanol. The stereochemistry of the two asymmetric carbon atoms in the isoxazolidine ring may be determined by conventional methods that include x-ray crystallography, nuclear magnetic resonance, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

The compounds of the invention can be synthesized starting with the reaction of an appropriate 2-imidazolylacetophenone precursor with N-methylhydroxylamine to furnish the corresponding nitrone derivative 1. The preparation of such nitrones is described in our copending application Ser. No. 900,856 filed Aug. 27, 1986 whose disclosure is incorporated herein by reference. Subsequent reaction of compound 1 with 1-alkene derivatives having 3 to 6 carbon atoms such as compounds 2 and 5 provides diastereomeric mixtures of the desired cis and trans-isoxazolidine compounds 3 and 6, respectively (Schemes I and II). When compound 3 ($R^1=4$-Cl, $R^2=H$) is treated with methanesulfonyl chloride the methanesulfonyloxy analog 4 is prepared. Reaction of the mesylate derivative 4 with an appropriate alcohol compound supplies the corresponding alkoxylkyl compound 3 (Scheme I).

(a) allyl cyclohexyl ether (2: $R^2=c$-$C_6H_{11}$ has a boiling point of 30°–35° C. (0.45 mm).

(b) allyl 4-tert-butylcyclohexyl ether [2: $R^2=c$-$C_6H_{10}C(CH_3)_3$-4] has a boiling point of 55°–60° C. (0.40 mm), and (c) allyl 4-chlorobenzyl ether (2: $\neq R^2=CH_2C_6H_4Cl$-4) has a boiling point of 60°–65° C. (0.06 mm).

Scheme I

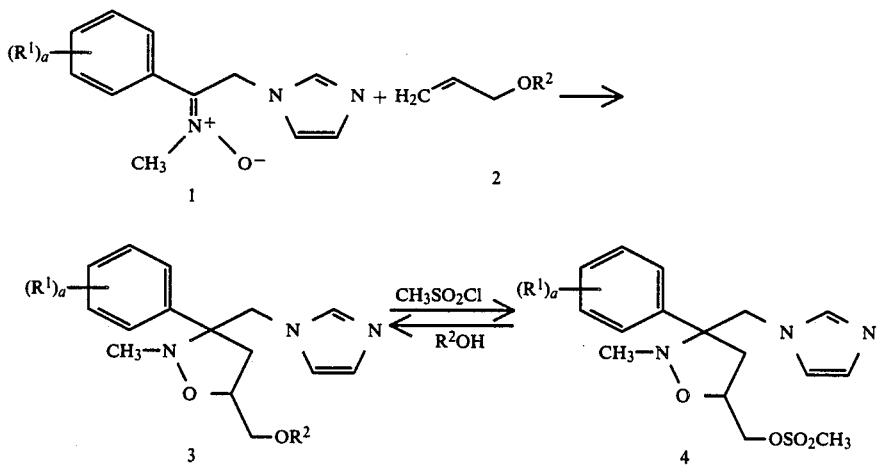

Scheme II

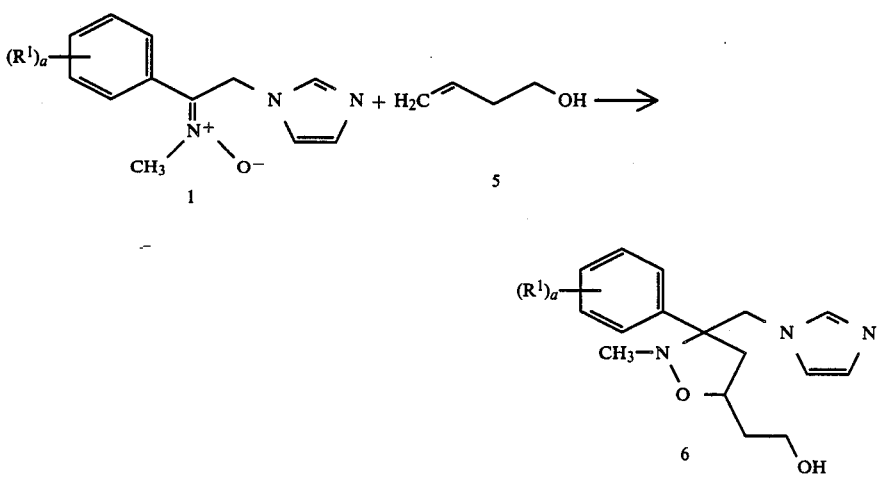

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following synthesis of intermediates and in the Examples.

PREPARATION OF ALLYL ETHERS

Allyl alcohol (2: $R^2=H$), 3-buten-1-ol (5) and 3-allyloxy-1,2-propanediol [2: $R^2=CH_2CH(OH)CH_2(OH)$] are commercially available. The remaining alkyl ethers (2) are prepared by standard literature procedures from appropriately substituted alkanol and allyl bromide, using sodium hydride as the base.

EXAMPLE 1

5-[(2,3-Dihydroxypropoxy)methyl]-3-phenyl-3-(1H-imidazol-1-ylmethyl)-2-methylisoxazolidine (3: $R^1=H$, $R^2=CH_2CH(OH)$—$CH_2OH$)

A solution of 7.88 g (36.6 mmol) of 1-phenyl-2-(1H-imidazol-1-yl)-N-methylethanimine N-oxide (1: $R^1=H$) [prepared by reacting 2-(1H-imidazol-1-yl)acetophenone (18.70 g, 0.10 mol), N-methylhydroxylamine hydrochloride (9.78 g, 0.117 mol), and $K_2CO_3$ (17.24 g, 0.125 mol) in 200 ml of ethanol and 5.40 ml (5.77 g, 43.6 mmol) of 3-allyloxy-1,2-propanediol [2: $R^2=CH_2CH(OH)CH_2OH$] in 150 ml of toluene is refluxed for 50 hours under a nitrogen atmosphere. Upon cooling to room temperature the solvent is removed under reduced pressure. The residual oil is crystallized from ethyl acetate to provide 6.21 g (49%) of compound 3 [$R^1=H$, $R^2=CH_2CH(OH)CH_2OH$], mp 99°–104° C.

Anal. Calcd for $C_{18}H_{25}N_3O_4$: C, 62.23; H, 7.25; N, 12.10. Found: C, 62.15; H, 7.22; N, 12.02.

EXAMPLE 2

5-[(Cyclohexyloxy)methyl]-3-(4-chlorophenyl)-3-(1H-imidazol-1-ylmethyl)-2-methylisoxazolidine (3: $R^1=4$-Cl, $R^2=$c-$C_6H_{11}$)

Derivative 3 ($R^1=4$-Cl, $R^2=$c-$C_6H_{11}$) is prepared by a procedure similar to that described in Example 1 by reacting 1-(4-chlorophenyl)-2-(1H-imidazol-1-yl)-N-methylethanimine N-oxide (1: $R^1=4$-Cl) with allyl cyclohexyl ether (2: $R_2=$c-$C_6H_{11}$). The resulting cis-/trans-diastereomeric mixture of compound 3 ($R^1=4$-Cl, $R^2=$c-$C_6H_{11}$) is flash-chromatographed on neutral silica gel using a 99:1 by volume mixture of chloroform-methanol as eluent.

Isomer A has a melting point of 122°–126° C. (ethyl acetate).

Anal. Calcd for $C_{21}H_{28}ClN_3O_2$: C, 64.69; H, 7.24; Cl, 9.09; N, 10.78. Found: C, 64.78; H, 7.30; Cl, 8.91; N, 10.74.

EXAMPLE 3

5-{[4-(1,1-Dimethylethyl)cyclohexyloxy]methyl}-3-(4-chlorophenyl)-3-(1H-imidazol-1-ylmethyl)-2-methylisoxazolidine (3: $R^1=4$-Cl, $R^2=$c-$C_6H_{10}C(CH_3)_3$-4)

Derivative 3 [$R^1=4$-Cl, $R^2=$c-$C_6H_{10}C(CH_3)_3$-4] is prepared by a procedure similar to that described in Example 1 by reacting 1-(4-chlorophenyl)-2-(1H-imidazol-1-yl)-N-methylethanimine N-oxide (1: $R^1=4$-Cl) with allyl 4-tert-butylcyclohexyl ether [2: $R^2=$c-$C_6H_{10}C(CH_3)_3$-4]. The resulting cis-/trans-diastereomeric mixture of compound 3 [$R^1=4$-Cl, $R^2=$c-$C_6H_{10}C(CH_3)_3$-4] is flash-chromatographed on neutral silica gel using chloroform-methanol (99:1 by volume) as eluent.

Isomer A has a melting point of 145°–148° C. (ethyl acetate).

Anal. Calcd for $C_{25}H_{26}ClN_3O_2$: C, 67.32; H, 8.14; Cl, 7.95; N, 9.42. Found: C, 67.44; H, 8.09; Cl, 8.32; N, 9.37.

EXAMPLE 4

5-{[(4-Chlorophenyl)methoxy]methyl}-3-(4-chlorophenyl)-3-(1H-imidazol-1-ylmethyl)-2-methylisoxazolidine (3: $R^1=4$-Cl, $R^2=CH_2C_6H_4Cl$-4)

Derivative 3 ($R^1=4$-Cl, $R^2=CH_2C_6H_4Cl$-4 is prepared by a procedure similar to that described in Example 1 by reacting 1-(4-chlorophenyl)-2-(1H-imidazol-1-yl)-N-methylethanimine N-oxide (1: $R^1=4$-Cl) with allyl 4-chlorobenzyl ether (2: $R^2=CH_2C_6H_4Cl$-4). The resulting cis-/trans-diastereomeric mixture of the title compound (3: $R^1=4$-Cl, $R^2=CH_2C_6H_4Cl$-4) is flash-chromatographed on neutral silica gel using chloroform-methanol (98:2 by volume) as eluent.

Isomer A has a melting point of 97°–100° C. (ethyl acetate hexane, 1:1 by volume). Anal. Calcd for $C_{22}H_{23}Cl_2N_3O_2$: C, 61.12; H, 5.36; Cl, 16.40; N, 9.72. Found: C, 61.04; H, 5.46; Cl, 16.56; N, 9.72.

EXAMPLE 5

5-(2-Hydroxyethyl)-3-(4-chlorophenyl)-3-(1H-imidazol-1-yl-methyl)-2-methylisoxazolidine (6: $R^1=4$-Cl)

Derivative 6 ($R^1=4$-Cl) is prepared by a procedure similar to that described in Example 1 by refluxing a solution of 16.98 g (68 mmol) of 1-(4-chlorophenyl)-2-(1H-imidazol-1-yl)-N-methylethanimine N-oxide (1: $R^1=4$-Cl) with 9.0 ml (7.49 g, 104 mmol) 3-buten-1-ol (5) in 150 ml of toluene for 28 hours under a nitrogen atmosphere. The reaction mixture is then cooled to room temperature. The resulting cis-/trans-diastereomeric mixture of compound 6 ($R^1=4$-Cl) is flash-chromatographed on neutral silica gel using chloroform-methanol (96:4 by volume) as eluent.

Isomer A has a melting point of 125°–130° C. (ethyl acetate).

EXAMPLE 6

5-(Hydroxymethyl)-3-(4-chlorophenyl)-3-(1H-imidazol-1-yl-methyl)-2-methylisoxazolidine (3: $R^1=4$-Cl, $R^2=H$)

Derivative 3 ($R^1=4$-Cl, $R^2=H$) is prepared by a procedure similar to that described in Example 1 by refluxing a solution of 24.97 g (100 mmol) of 1-(4-chlorophenyl)-2-(1H-imidazol-1-yl)-N-methylethanimine N-oxide (1: $R^1=4$-Cl) with 14.0 ml (11.95 g, 200 mmol) of allyl alcohol (2: $R^2=H$) in 300 ml of toluene for 19 hours under a nitrogen atmosphere. The reaction mixture is then cooled to room temperature and the solvent removed under reduced pressure. The resulting cis-/trans-diastereomeric mixture of compound 3 ($R^1=4$-Cl, $R^2=H$) is flash-chromatographed on neutral silica gel using as eluent a 9:1 by volume mixture of chloroform-methanol.

Isomer A has a melting point of 169°–170° C. (isopropanol).

Anal. Calcd for $C_{15}H_{18}ClN_3O_2$: C, 58.54, H, 5.89; Cl, 11.52; N, 13.65. Found: C, 58.42; H, 5.88; Cl, 11.51; N, 13.57.

EXAMPLE 7

5-(Methoxymethyl)-3-(4-chlorophenyl)-3-(1H-imidazol-1-yl-methyl)-2-methylisoxazolidine (3: $R^1=4$-Cl, $R^2=CH_3$)

5-(Hydroxymethyl)-3-(4-chlorophenyl)-3-(1H-imidazol-1-ylmethyl)-2-methylisoxazolidine (3: $R^1=4$-Cl, $R^2=H$) 2.50 g, 8 mmol) is added to a suspension of 1.32 g (24 mmol) of 50% by weight sodium hydride in 50 ml anhydrous tetrahydrofuran, at 0° C. under a nitrogen atmosphere. After stirring for 1 hour at 0° C., 1.28 g (9 mmol) of methyl iodide is added and the resulting suspension is heated to reflux and stirred for 20 hours. Upon cooling to room temperature, the reaction mixture is poured into 100 ml of water and then extracted with chloroform (3×75 ml). The combined organic extracts are dried over anhydrous magnesium sulfate and the solvent removed under reduced pressure. The crude residue is flash-chromatographed on neutral silica gel using chloroform-methanol (98:2 by volume) as eluent. Following crystallization from ethyl acetate, 1.67 g (64%) of compound 3 ($R^1=4$-Cl, $R^2=CH_3$) are obtained, mp 123°–126° C.

Anal. Calcd for $C_{16}H_{20}ClN_3O_2$: C, 59.72; H, 6.26; N, 13.06. Found: C, 59.71; H, 6.33; N, 12.98.

EXAMPLE 8

5-[(2-Propenoxy)methyl]-3-(4-chlorophenyl)-3-(1H-imidazol-1-ylmethyl)-2-methylisoxazolidine (3: $R^1=4$-Cl, $R^2=CH_2CH=CH_2$)

Derivative 3 ($R^1=4$-Cl, $R^2=CH_2CH=CH_2$) is prepared by a procedure similar to that described in Example 7 by reacting 5-(hydroxymethyl)-3-(4-chlorophenyl)-3-(1H-imidazol-1-yl-methyl)-2-methylisoxazolidine (3: R¹=4-Cl, R²=H) with allyl bromide. Compound 3 (R¹=4-Cl, R²=CH₂CH=CH₂) is isolated by flash-chromatography on neutral silica gel using as eluent a 98:2 by volume mixture of chloroform-methanol, mp 89°-92° C. (ethyl acetate). Anal. Calcd for C₁₈H₂₂ClN₃O₂: C, 62.15; H, 6.38; Cl, 10.19; N, 12.08. Found: C, 61.94; H, 6.35; Cl, 10.29; N, 11.95.

EXAMPLE 9

5-[(Methanesulfonyloxy)methyl]-3-(4-chlorophenyl)-3-(1H-imidazol-1-ylmethyl)-2-methylisoxazolidine (4: R¹=4-Cl)

Methanesulfonyl chloride (4.17 ml, 54 mmol) is added dropwise, at 0° C. under a nitrogen atmosphere, to a solution of 12.50 g (41 mmol) of 5-(hydroxymethyl)-3-(4-chlorophenyl)-3-(1H-imidazol-1-ylmethyl)-2-methylisoxazolidine (3: R¹=4-Cl, R²=H) in 100 ml of anhydrous pyridine. After stirring for 4.5 hours at 0° C., the reaction mixture is warmed to room temperature and diluted with water. Then, the reaction mixture is neutralized by cautious addition of 12.04 g potassium carbonate and extracted with methylene chloride (3×75 ml). The combined organic extracts are dried over anhydrous magnesium sulfate and the solvent is removed under reduced pressure leaving 14.98 g (95%) of compound 4 (R¹=4-Cl), mp 159°-162° C. (chloroform-petroleum ether, 1:1 by volume). Anal. Calcd for C₁₆H₂₀ClN₃O₄S: C, 49.80; H, 5.22; N, 10.89. Found: C, 49.46; H, 5.13; N 10.81.

EXAMPLE 10

5-(Ethoxymethyl)-3-(4-chlorophenyl)-3-(1H-imidazol-1-yl-methyl)-2-methylisoxazolidine (3: R¹=4-Cl, R²=CH₂CH₃)

To a solution of sodium ethoxide in ethanol [prepared from 1.16 g (50 mmol) of sodium metal and 50 ml ethanol] is added under a nitrogen atmosphere 3.56 g (9.2 mmol) of 5-[(methanesulfonyloxy)methyl]-3-(4-chlorophenyl)-3-(1H-imidazol-1-ylmethyl)-2-methylisoxazolidine (4: R¹=4-Cl). The resulting solution is refluxed for 3 hours, then cooled to room temperature, poured into 200 ml ice-water, and extracted with chloroform (3×100 ml). The organic layer is dried over anhydrous magnesium sulfate and the solvent is removed under reduced pressure. The crude residue is flash-chromatographed on neutral silica gel using a 98:2 by volume mixture of chloroform-methanol as eluent, to give 1.82 g (59%) of compound 3 (R¹=4-Cl, R²=CH₂CH₃), mp 147°-149° C. (ethyl acetate). Anal. Calcd for C₁₇H₂₂ClN₃O₂: C, 60.80; H, 6.60; N, 12.51. Found: C, 60.86; H, 6.66; N, 12.48.

EXAMPLE 11

5-(n-Butoxymethyl)-3-(4-chlorophenyl)-3-(1H-imidazol-1-yl-methyl)-2-methylisoxazolidine (3: R¹=4-Cl, R²=(CH₂)₃—CH₃)

Derivative 3 [R¹=4-Cl, R²=(CH₂)₃CH₃] is prepared by a procedure similar to that described in Example 10 by reacting 5-[(methanesulfonyloxy)methyl]-3-(4-chlorophenyl)-3-(1H-imidazol-1-ylmethyl)-2-methylisoxazolidine (4: R¹=4-Cl) with sodium n-butoxide. Compound 3 [R¹=4-Cl, R²=(CH₂)₃CH₃] is isolated by flash-chromatography on neutral silica gel using as eluent a 98:2 by volume mixture of chloroform-methanol, mp 53°-56° C. (ethyl acetate-petroleum ether, 1:1 by volume). Anal. Calcd for C₁₉H₂₆ClN₃O₂:

C, 62.71; H, 7.20; Cl, 9.74; N, 11.55. Found: C, 62.56; H, 7.14; Cl, 9.82; N, 11.51.

Other compounds of the invention where R¹ includes mono- or disubstitution with halogen, lower alkyl and-/or lower alkoxy are prepared starting with nitrones 1 formed from imidazolylacetophenones such as:

2-(1H-imidazol-1-yl)-4'-methylacetophenone, mp 133°-137° C., 2-(1H-imidazol-1-yl)-4'-methoxyacetophenone, mp 134°-137° C., 2-(1H-imidazol-1-yl)-4'-fluoroacetophenone, mp 150°-155° C., 2-(1H-imidazol-1-yl)-3',4'-dichloroacetophenone, mp 124°-126° C., 2-(1H-imidazol-1-yl)-4'-chloro-3'-methylacetophenone, mp 116°-118° C., 2-(1H-imidazol-1-yl)-3'-methoxyacetophenone, mp 111°-113° C., and 2-(1H-imidazol-1-yl)-3'-methylacetophenone.

Salts of the compounds of the invention can be prepared as known in the art, for example, by dissolving the compound in a 10:1 by volume mixture of ethanol and an aqueous acid such as HCl or HNO₃, evaporating the solvent, and then recrystallizing the crude salt, for example, from methanol-ether, 1:3 by volume in the case of HCl salts, and ethanol in the case of HNO₃ salts.

We claim:

1. A compound of the formula:

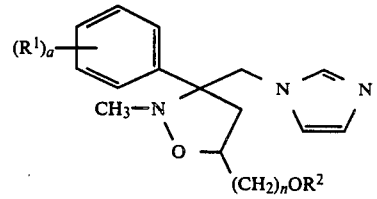

or a pharmaceutically acceptable acid addition salt thereof, in the form of their enantiomers, or mixtures of their enantiomers including diastereoisomeric pairs of such enantiomers, wherein, a=1 or 2, R¹ is selected from hydrogen, lower alkyl, lower alkoxy, halogen and combinations thereof, provided that the ortho position is hydrogen, R² is selected from hydrogen, lower alkyl, mono- or dihydroxy-substituted lower alkyl, allyl, cyclohexyl, lower alkyl-substituted cyclohexyl, methanesulfonyl and (halophenyl)methyl, and the alkyl moiety (CH₂)ₙ represents a chain where n=1 to 4.

2. The compound of claim 1 wherein the compound is 5-[2,3-dihydroxypropoxy)methyl]-3-phenyl-3-(1H-imidazol-1-ylmethyl)-2-methylisoxazolidine.

3. The compound of claim 1 wherein the compound is 5-{[4-(1,1-dimethylethyl)cyclohexyloxy]methyl}-3-(4-chlorophenyl)-3-(1H-imidazol-1-ylmethyl)-2-methylisoxazolidine.

4. The compound of claim 1 wherein the compound is 5-{[(4-chlorophenyl)methoxy]methyl}-3-(4-chlorophenyl)-3-(1H-imidazol-1-ylmethyl)-2-methylisoxazolidine.

5. The compound of claim 1 wherein the compound is 5-(2-hydroxyethyl)-3-(4-chlorophenyl)-3-(1H-imidazol-1-ylmethyl-2-methylisoxazolidine.

6. The compound of claim 1 wherein the compound is 5-(hydroxymethyl)-3-(4-chlorophenyl)-3-(1H-imidazol-1-yl-methyl)-2-methylisoxazolidine.

7. The compound of claim 1 wherein the compound is 5-(methoxymethyl)-3-(4-chlorophenyl)-3-(1H-imidazol-1-yl-methyl)-2-methylisoxazolidine.

8. The compound of claim 1 wherein the compound is 5-[(2-propenoxy)methyl]-3-(4-chlorophenyl)-3-(1H-imidazol-1-ylmethyl)-2-methylisoxazolidine.

9. The compound of claim 1 wherein the compound is 5-[(methanesulfonyloxy)methyl]-3-(4-chlorophenyl)-3-(1H-imidazol-1-ylmethyl)-2-methylisoxazolidine.

10. The compound of claim 1 wherein the compound is 5-(ethoxymethyl)-3-(4-chlorophenyl)-3-(1H-imidazol-1-yl-methyl)-2-methylisoxazolidine.

11. The compound of claim 1 wherein the compound is 5-(n-butoxymethyl)-3-(4-chlorophenyl)-3-(1H-imidazol-1-yl-methyl)-2-methylisoxazolidine.

12. The compound of claim 1 wherein the compound is 5-[(cyclohexyloxy)methyl]-3-(4-chlorophenyl)-3-(1H-imidazol-1-ylmethyl)-2-methylisoxazolidine.

* * * * *